United States Patent [19]

Lira et al.

[11] 3,953,597

[45] Apr. 27, 1976

[54] USE OF 6-AMINO-9-(SUBSTITUTED BENZYL)PURINES AND THEIR CORRESPONDING N$^1$-OXIDES AS COCCIDIOSTATS

[75] Inventors: Emil P. Lira, Des Plaines; Walter M. Barker, Mundelein; Robert C. McCrae, Lake Zurich, all of Ill.

[73] Assignee: International Minerals & Chemical Corporation, Libertyville, Ill.

[22] Filed: Aug. 9, 1974

[21] Appl. No.: 496,027

Related U.S. Application Data

[60] Division of Ser. No. 219,848, Feb. 4, 1972, Pat. No. 3,846,426, which is a continuation-in-part of Ser. No. 120,781, March 3, 1971, abandoned.

[52] U.S. Cl. ............................. 424/253; 260/252
[51] Int. Cl.$^2$ ........................................ A61K 31/52
[58] Field of Search ................................... 424/253

[56] References Cited
OTHER PUBLICATIONS
Schaeffer et al., — J. of Med. Chem. Vol. 13, (1970), pp. 452–455.

*Primary Examiner*—Sam Rosen
*Attorney, Agent, or Firm*—Peter Andress; James E. Wolber

[57] ABSTRACT

Novel 6-amino-9-(substituted benzyl)purines are prepared by allowing an appropriate substituted benzyl halide, e.g., a substituted benzyl chloride, to react with adenine under the appropriate conditions. Oxidation of the resulting purine derivatives yields the corresponding N$^1$-oxides. These compounds, i.e., both the purine derivatives and the N$^1$-oxides thereof, have anti-coccidial activity and are useful for controlling cecal and/or intestinal coccidiosis when administered in minor quantities to animals, in particular to poultry, usually in admixture with animal sustenance.

43 Claims, No Drawings

USE OF 6-AMINO-9-(SUBSTITUTED BENZYL)PURINES AND THEIR CORRESPONDING N¹-OXIDES AS COCCIDIOSTATS

CROSS-REFERENCE TO RELATED APPLICATIONS

This is a division of application Ser. No. 219,848, filed Feb. 4, 1972, now U.S. Pat. No. 3,846,426, which is a continuation-in-part of application Ser. No. 120,781, filed Mar. 3, 1971, now abandoned.

BACKGROUND OF THE INVENTION

This invention relates to new chemical compounds and the method of the preparation of the same. It relates further to the use of new compounds for treating and preventing coccidiosis. This invention still more particularly relates to novel 6-amino-9-(substituted benzyl)purines and their corresponding N¹-oxides, and the use of the same in the control and treatment of coccidiosis.

Coccidiosis is a widespread poultry disease which is produced by infections of protozoa of the genus *Eimeria* which causes severe pathology in the intestines and ceca of poultry. Some of the most significant of these species are *E. tenella*, *E. acervulina*, *E. necatrix*, *E. brunetti* and *E. maxima*. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

SUMMARY OF THE INVENTION

This invention is based on the discovery that certain novel 6-amino-9-(substituted benzyl)purines, as well as their corresponding N¹-oxides, have a surprisingly and unexpectedly high degree of activity against coccidiosis of poultry. Administering a small amount of at least one of these compounds, preferably in combination with poultry feed, is effective to prevent or greatly reduce the incidence of coccidiosis. The compounds are effective against both the cecal form (caused by *E. tenella*) and the intestinal forms (principally caused by *E. acervulina*, *E. brunetti*, *E. maxima* and *E. necatrix*). The coccidiostats of this invention are particularly effective against the species that cause intestinal damage. In addition to preventing the pathology caused by coccidia, these compounds also exert an inhibitory effect on the oocysts by greatly reducing the number and/or the sporulation of those produced.

The novel purine derivatives of this invention are prepared by reacting an appropriate substituted benzyl halide and adenine in the presence of a base in a suitable reaction medium to obtain a novel 6-amino-9-(substituted benzyl)purine along with other isomers. The 9-isomer thus formed, either isolated or in the mixture with the other isomers, is then subjected to a suitable oxidizing agent such as hydrogen peroxide, or a peraromatic or peraliphatic acid, to produce the novel corresponding 6-amino-9-(substituted benzyl)-purine-N¹-oxide of this invention.

It is, therefore, a primary object of this invention to provide novel 6-amino-9-(substituted benzyl)purines and their corresponding N¹-oxides which are useful in the control of coccidiosis.

Another object of this invention is to provide novel anti-coccidial agents.

Still another object of this invention is to provide novel feed compositions useful for the prevention and suppression of coccidiosis in poultry.

A further object of this invention is to provide a new and useful method for the control of coccidiosis in poultry which comprises administering to the poultry minor amounts of the anti-coccidial substances of this invention.

A still further object of the invention is to provide a method for preparing novel 6-amino-9-(substituted benzyl)-purines and their corresponding N¹-oxides.

These and further objects of this invention will become apparent or be described as the description thereof herein proceeds.

DESCRIPTION OF THE PREFERRED EMBODIMENTS

In accordance with this invention, coccidiosis in poultry is controlled or suppressed by administering to the poultry a non-toxic, anti-coccidially effective quantity of a compound of the structural formula:

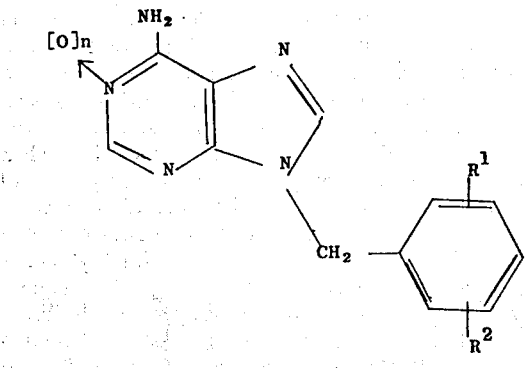

wherein $n$ is 0 or 1, and (a) $R^1$ and $R^2$, independently are of the group consisting of hydrogen, halogen, i.e., chlorine, bromine, iodine or fluorine, nitro, and trihalomethyl, provided that at least one of such substituents is other than hydrogen and no more than one of such substituents is of the group consisting of nitro and trihalomethyl, and $R^1$ and $R^2$ are located in the 2 and 6 positions on the carbocyclic portion of the compound, or (b) $R^1$ and $R^2$ are both methyl and are located in the 3 and 4 positions on the carbocyclic ring. Preferred compounds are those where one of the substituents $R^1$ and $R^2$ is hydrogen or where both of the substituents are halogen, either the same or different, or methyl. Specific examples of novel compounds represented by the foregoing structural formula are 6-amino-9-(2-chlorobenzyl)purine; 6-amino-9-(3,4-dimethylbenzyl)-purine; 6-amino-9-(2-nitrobenzyl)purine; 6-amino-9-(2-bromobenzyl)purine; 6-amino-9-(2,6-dibromobenzyl) purine; 6-amino-9-(2-iodobenzyl)purine; 6-amino-9-(2-trifluoromethylbenzyl)purine; 6-amino-9-(2-chloro-6-iodobenzyl)purine and 6-amino-9-(2-chloro-6-bromobenzyl)purine; and their corresponding N¹- oxides. The most preferred compounds are 6-amino-9-(2,6-dichlorobenzyl)purine and 6-amino-9-(2-chloro-6-fluorobenzyl)purine and their corresponding $N^1$-oxides, 6-amino-9-(2,6-dichlorobenzyl)purine-$N^1$-oxide and 6-amino-9-(2-chloro-6-fluorobenzyl)purine-$N^1$-oxide, respectively.

In preparing the novel coccidiostats of this invention, the appropriate substituted benzyl halide (i.e., chloride, bromide, iodide or fluoride) is initially contacted with adenine in a suitable reaction medium, and the resulting reaction mixture is maintained to permit the reaction to take place. Useful benzyl halides may be characterized as those that are substituted so as to produce the novel compounds as hereinbefore described upon reaction with adenine, that is, benzyl halides containing one or two substituents of the group consisting of halogen, nitro and trihalomethyl in the 2 and 6 positions of the ring portion, provided no more than one of the substituents is of the group consisting of nitro and trihalomethyl, or containing methyl substituents in each of the 3 and 4 positions, with preferred benzyl halides being those containing only one of the aforementioned substituents in the 2-position (i.e., halogen, nitro and trihalomethyl) or containing two halogens or two methyl radicals. Benzyl halides that are useful in the preparation of the coccidiostats of this invention include 2,6-dichlorobenzyl chloride, 2-bromobenzyl bromide, 2-iodobenzyl bromide, 3,4-dimethylbenzyl chloride, 2-nitrobenzyl chloride, 2-chlorobenzyl chloride, and 2-chloro-6-fluorobenzyl bromide.

Suitable reaction media include both protic and aprotic solvents that are inert, i.e., non-reactive with the components of the reaction mixture under the reaction conditions that are maintained. Examples of such solvents include dialkyl alkanoamides, such as dimethyl formamide and dimethyl acetamide, alcohols, such as ethanol, propanol, isopropanol, butanol, amyl alcohol, cyclohexanol and benzyl alcohol, including aqueous systems containing up to about 50 percent of an alcohol such as previously characterized, dimethyl sulfoxide, ethylene glycol and diethylene glycol. In general any of the solvents which are disclosed in the art as being useful in the base-catalyzed alkylation of adenine may be used in the first step of this invention for preparing the novel coccidiostats.

The bases that are useful for catalyzing the reaction between the substituted benzyl halide and adenine are those disclosed in the art as being useful for catalyzing the alkylation of adenine. In general, suitable bases include all of those that have sufficient basicity to generate the adenine anion in the solvent system used. Examples of suitable bases include carbonates, e.g., alkali metal carbonates such as sodium carbonate and potassium carbonate, hydroxides, e.g., alkali metal hydroxides such as sodium hydroxide, potassium hydroxide and lithium hydroxide, tertiary amines, e.g., trimethyl amine, triethyl amine, tripropyl amine and dimethyl analine, and alcoholates, e.g., potassium ethoxide, sodium ethoxide, potassium t-butoxide and sodium ethylate. Preferred bases are those having a $pK_b$ greater than 10.5 so that the adenine is substantially completely converted to its anion.

The relative proportions of the components of the reaction mixture of the first step may vary over a relatively wide range. The reactants may be used in stoichiometric amounts, i.e., equal moles of the two reactants may be used, or an excess, e.g., a 10% or even greater molar excess, of either of the reactants may also be used. The quantity of the base is similarly not critical and may vary over a wide range, but it is preferably used in at least stoichiometric amount with a slight excess being most preferred. The amount of the solvent used may also vary over a wide range. The solvent is used in a quantity sufficient to permit the reaction to proceed at a reasonable rate and facilitate isolation of the reaction product.

The reactants and the base catalyst are combined in the reaction medium in any conventional manner and in any order. As illustrative of a suitable manner of combining the components of the reaction mixture, the adenine is added to a solution of the base in the reaction medium, after which the substituted benzyl halide is then added, either neat or in a suitable solvent. Other methods of combining the reactants and catalyst will be obvious but it is preferred that they be combined so that the anion of the adenine forms no later than the time the benzyl halide is added and most preferably prior to such time, i.e., the benzyl halide is most preferably added last.

The reaction time and temperature conditions are not unduly critical. The time of the reaction will, however, decrease as the reaction temperature increases. The reaction will most conveniently be conducted between a temperature in the range of from about 50° to about 100° C. However, substantially lower temperatures may be used so long as the reaction system is maintained in the liquid state. The reaction may be conducted at temperatures substantially higher than 100° C. provided the temperature is maintained at a level below that at which the components of the reaction mixture will decompose.

The reactants are thus contacted with each other in the presence of the base in the reaction medium to insure completion of the reaction. The product of the reaction, i.e., the 6-amino-9-(substituted benzyl)purine, either as a pure compound or along with the other isomers that form, e.g., the 1-,3-, and 7-isomers, will either remain entirely in solution or precipitate after awhile, depending upon the quantity of solvent utilized, as hereinbefore outlined. Upon completion of the reaction, the reaction mixture may be cooled, e.g., to a temperature of about 0° C, to precipitate a solid product or to precipitate a further quantity of this product. The product is then isolated in the usual manner, such as by filtration, and, if desired, purified by conventional methods such as washing with ethanol or water and recrystallizing from a suitable solvent such as acetic acid, aqueous acetic acid, dimethyl formamide or dimethyl sulfoxide. The 6-amino-9-(substituted benzyl)-purine can be purified if it is used in that form as a coccidiostat in accordance with this invention instead of being first converted to the corresponding $N^1$-oxide.

The 6-amino-9-(substituted benzyl)purine thus obtained from the initial reaction may readily be converted to the corresponding novel purine-$N^1$-oxide of this invention by subjecting the same to the action of a suitable oxidizing agent. This is accomplished by initially dissolving the crude reaction product or isolated 9-isomer in a suitable acidic solvent, inorganic or organic, such as sulfuric acid, acetic acid, formic acid or butyric acid, dioxane, aqueous dioxane or ethylene glycol, and then adding an oxidizing agent that is compatible with the solvent. Oxidizing agents which may be used include hydrogen peroxide, peraromatic acids such as perbenzoic and metachloroperbenzoic acids, and peralphatic acids such as peracetic and pertrifluoroacetic acids. The oxidizing mixture is either allowed to stand or is heated for a time sufficient to permit the oxidizing reaction to substantially go to completion. Solid 6-amino-9-(substituted benzyl)purine-N$^1$-oxide, but not corresponding oxidized products of the other isomers, e.g., the 1-, 3- and 7-isomers, is then recovered by cooling the oxidizing mixture to precipitate the product, or other suitable known methods of isolation may be used. Oxidized products of isomers other than the 9-isomers are not recovered, apparently since the other isomers are not oxidized or, if they are oxidized, the products thus formed are not easily isolated or they undergo further reactions to form other compounds that are not recovered with the oxidized 9-isomers. The crude product thus obtained is usually further purified by conventional methods such as recrystallization from an organic acid such as acetic acid.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum is sufficient to control coccidiosis and the maximum amount is such that the coccidiostat does not result in any undesirable effects.

A feed will typically contain from about 0.0005 to about 0.05 percent, preferably from about 0.0025 to about 0.01 percent by weight of one of the coccidiostats of this invention. The optimum levels will naturally vary with the specific compound utilized and species of Eimeria involved, and can be readily determined by one skilled in the art. Levels of 6-amino-9-(2,6-dichlorobenzyl)purine and its corresponding N$^1$-oxide, which are among the most preferred coccidiostats of this invention, in poultry feed of from about 0.0035 percent to about 0.0075 percent by weight of the diet are especially useful in controlling the pathology associated with E. tenella, while the preferred concentration for similar control of intestinal-dwelling species is from about 0.0025 percent to about 0.0065 percent by weight of the diet. Amounts of about 0.0045 percent and 0.0065 percent by weight for 6-amino-9-(2,6-dichlorobenzyl)purine and 6-amino-9-(2,6-dichlorobenzyl)purine-N$^1$-oxide, respectively, are advantageous in reducing the pathogenic effects of both cecal and intestinal coccidiosis.

Depending on the compound employed, levels of 0.001 percent to 0.0035 percent possess the novel effects of reducing the number of oocysts passed in the droppings of infected chickens and/or inhibiting the subsequent division and maturation to infectivity, scientifically designated as the process of sporulation. Thus, the combination of prevention of pathology, coupled with the inhibiting effect on the reproductive product of these organisms, the oocysts, present a unique two-fold method for the control of coccidiosis in poultry.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE I

The compound 6-amino-9-(2,6-dichlorobenzyl)purine was initially prepared by slowly adding about 67.5 grams (0.5 mole) of dry adenine to a solution of about 57 grams (0.5 mole) potassium t-butoxide in one liter of absolute ethanol. This mixture was stirred for about two hours, and then about 97.5 grams (0.5 mole) of 2,6-dichlorobenzyl chloride was added over a period of about 4 hours. The resulting mixture was heated to reflux with stirring and allowed to react for about 42 hours, after which it was cooled to about −10°C. The crude 6-amino-9-(2,6-dichlorobenzyl)purine thus formed was isolated by filtration and then washed with ice cold ethanol and ice cold water to yield 118 grams of a crude product.

The crude 6-amino-9-(2,6-dichlorobenzyl)purine obtained from the initial reaction was dissolved in one liter of acetic acid. A 30% aqueous solution of hydrogen peroxide was then added in the amount of 350 milliliters. The solution was allowed to stand for 5 days at room temperature, after which about 400 milliliters of water was added and the solution was cooled. The resulting precipitate was recovered by filtration, reslurried in 500 milliliters of a 30% aqueous solution of acetic acid, and then in one liter of water. The solids recovered from the aqueous slurry were vacuum dried to yield 75 grams of a crude 6-amino-9-(2,6-dichlorobenzyl)purine-N$^1$-oxide having a melting point of 296°–301° C, representing a 40 percent yield. An analytical sample of the same having a melting point of 298°–302° C. was prepared by recrystallization from acetic acid.

EXAMPLE II

White Rock cockerels obtained from a commercial hatchery as day-old chicks were raised in a manner to prevent exposure to extraneous coccidial infection until they were fourteen days old. When the chicks were fourteen days old, they were individually weighed and divided into groups of ten each so that each group was substantially uniform in chick size and mean weight. The test compound, 6-amino-9-(2,6-dichlorobenzyl)purine-N$^1$-oxide prepared as described in Example I, was thoroughly dispersed in separate quantities of a vitamin K-deficient mash diet in concentrations of 0.01, 0.0075, 0.005, 0.0025 and 0.001% by weight. Each of these rations was offered ad libitium to a group of chicks. Other groups of chicks were fed the same mash diet without the addition of the test compound. Two days after this diet was started, all but three groups (30 chicks), designated the uninfected or normal control (UIC), were inoculated orally into the crop with 100,000 sporulated oocysts of E. tenella. Two of the groups (20 chicks) which were so inoculated were fed to the mash diet without any test compound so as to serve as the infected or positive control (IC). The experiment was terminated six days after the chicks were inoculated.

Mortalities and fecal scores were recorded throughout the experiment. The fecal score was a grading on the extent of blood passed with droppings, using the following rating scale:

0 = None
1 = less than 10 percent
2 = 10 percent to 50 percent
3 = 0 Over 50 percent Oocysts counts were also obtained during the last two days of the tests by microscopic examination of the droppings to determine the average number of oocysts passed per chick. At the end of the test, weight gains and micro-hematocrits were determined. In determining the micro-hematocrits, a blood sample was collected from each chick with a heparinized micro-capillary tube which was then centrifuged to determine the present by volume of packed blood cells.

The results of this experiment are given in Table I.

TABLE I

| Medication % by wt. of Diet | No. of Chicks | % wt. Gain To UIC | % wt. Gain to IC | % Hematocrit | % Mortality | Fecal Score | Oocyst Count (×10⁶) |
|---|---|---|---|---|---|---|---|
| none, UIC | 30 | 100 | 181.9 | 31 | 0 | 0 | 0 |
| None, IC | 20 | 55.0 | 100 | 30 | 70 | 3.0 | 25.64 |
| 0.001 | 10 | 85.3 | 155.2 | 27 | 70 | 2.7 | 42.32 |
| 0.0025 | 10 | 37.9 | 69.0 | 27 | 40 | 2.3 | 56.95 |
| 0.005 | 10 | 86.3 | 156.9 | 28 | 0 | 2.3 | 31.0 |
| 0.0075 | 10 | 100.0 | 181.9 | 30 | 0 | 0.7 | 4.96 |
| 0.01 | 10 | 73.5 | 133.6 | 34 | 0 | 0 | 0.11 |

EXAMPLE III

This experiment was conducted substantially as outlined in Example II except that the chicks were inoculated with 3,000,000 sporulated oocysts of E. acervulina. The observations were limited to weight gains, fecal scores and oocysts counts. Fecal scores were based on the amount of mucus and consistency instead of on the blood in droppings, using the rating scale outlined in Example II.

The results of this experiment are outlined in Table II as follows:

TABLE II

| Medication % by wt. of Diet | No. of Chicks | % wt. Gain To UIC | % wt. Gain To IC | Fecal Score | Oocyst Count (×10⁶) |
|---|---|---|---|---|---|
| None, UIC | 30 | 100 | 159.8 | 0 | 0 |
| None, IC | 20 | 62.6 | 100 | 2.5 | 14.15 |
| 0.001 | 10 | 55.9 | 89.4 | 2.7 | 14 |
| 0.0025 | 10 | 71.6 | 114.4 | 1.7 | 17.0 |
| 0.005 | 10 | 93.8 | 150.0 | 0 | 1.22 |
| 0.0075 | 10 | 89.6 | 143.2 | 0 | 0 |
| 0.01 | 10 | 77.7 | 124.2 | 0 | 0.23 |

EXAMPLE IV

The procedure used in Example II was again followed except that the chicks were infected with five species of Eimeria simultaneously. Each chick was inoculated with a total of 510,000 sporulated oocysts consisting of 10,000 E. tenella, 200,000 E. acervulina, 50,000 E. necatrix, 100,000 E. brunetti, and 150,000 E. maxima. Table III which follows outlines the results of this experiment.

TABLE III

| Medication % by wt. of Diet | No. of Chicks | % wt. Gain To UIC | % wt. Gain To IC | % Hematocrit | % Mortality | Fecal Score | Oocyst Count (×10⁶) |
|---|---|---|---|---|---|---|---|
| None, UIC | 30 | 100 | 458.7 | 31 | 0 | 0 | 0 |
| None, IC | 20 | 21.8 | 100 | 24 | 50 | 3.0 | 24.30 |
| 0.001 | 10 | 29.8 | 137.0 | 20 | 60 | 3.0 | 32.55 |
| 0.0025 | 10 | 73.9 | 339.1 | 27 | 40 | 2.7 | 47.02 |
| 0.005 | 10 | 93.8 | 430.4 | 29 | 0 | 0.7 | 3.18 |
| 0.0075 | 10 | 92.9 | 426.1 | 32 | 0 | 0 | 0.24 |
| 0.01 | 10 | 83.4 | 382.6 | 31 | 0 | 0.3 | 0 |

EXAMPLE V

The general procedure outlined in Example II was again followed in this experiment, which was conducted to compare the effectiveness of the test compound, i.e., 6-amino-9-(2,6-dichlorobenzyl)purine-$N^1$-oxide, with five commercially available coccidiostats.

The test compound of this invention was administered to the chicks at 0.0065 percent by weight of the diet and was compared against the compounds listed below along with the dietary concentrations utilized.

| Compound | % by wt. in Diet | Chemical Name |
|---|---|---|
| A | 0.0125 | 1-(4-amino-2-N-propyl-5-pyrinidinyl-methyl)-2-picolinium chloride.hydrochloride |
| B | 0.0125 & 0.0004 | Compound A plus Methyl-4-acetamide-2-ethoxybenzoate |
| C | 0.00825 | Ethyl-4-hydroxy-6,7-diisobutoxy-3-quinoline-carboxylate |
| D | 0.0125 | 3,5-dichloro-2,6-dimethyl-4-pyridinol |

-continued

| Compound | % by wt. in Diet | Chemical Name |
|---|---|---|
| E | 0.0125 | 3,5-dinitro-O-toluamide. |

The compounds were administered to the chicks in feed for a total of nine days, which was the extent of this experiment. The chicks were inoculated, as in the previous examples, two days after the experiment started. All of the compounds were evaluated against individual infections of each of five species of Eimeria and a mixture of the five species given simultaneously. The species utilized and number of sporulated oocysts administered are listed below:

| | Individual Infection of One Species | Mixed Infection Of Five Species |
|---|---|---|
| E. tenella | 75,000 | 10,000 |
| E. acervulina | 2,000,000 | 200,000 |
| E. necatrix | 200,000 | 50,000 |
| E. brunetti | 200,000 | 100,000 |
| E. maxima | 240,000 | 150,000 |
| Total | | 510,000 |

The severity of the infections was evaluated, again utilizing an uninfected or normal control (UIC) and an infected or positive control (IC). There were 20 chicks in both of these control groups and ten in each of the remaining groups to which the test coccidiostats were administered. The criteria used in evaluating the effectiveness of the six anti-coccidial preparations being tested include weight gains with at least one of the following observations: percent mortality, percent hematocrit and/or fecal score, as outlined in Example II.

The results of this experiment are presented in Table IV as follows:

TABLE IV

| | None UIC | None IC | Test Compound | Commercial Coccidiostats A | B | C | D | E |
|---|---|---|---|---|---|---|---|---|
| E. tenella | | | | | | | | |
| % wt. gain to UIC | 100.0 | 49.3 | 95.2 | 99.3 | 96.8 | 97.3 | 97.3 | 96.6 |
| % wt. gain to IC | 202.8 | 100.0 | 193.1 | 201.4 | 195.8 | 197.2 | 197.2 | 195.8 |
| % Mortality | 0 | 55.0 | 0 | 0 | 0 | 0 | 0 | 0 |
| % Hematocrit | 30 | 20 | 30 | 28 | 28 | 28 | 30 | 30 |
| E. acervulina | | | | | | | | |
| % wt. gain to UIC | 100.0 | 45.3 | 100.0 | 89.0 | 98.3 | 100.0 | 86.6 | 54.6 |
| % wt. gain to IC | 220.5 | 100.0 | 220.5 | 196.2 | 216.7 | 220.5 | 191.0 | 120.5 |
| Fecal Score | 0 | 3 | 0 | 3 | 0 | 1 | 1 | 3 |
| E. necatrix | | | | | | | | |
| % wt. gain to UIC | 100.0 | 39.2 | 95.6 | 56.0 | 72.8 | 70.2 | 93.7 | 57.0 |
| % wt. gain to IC | 254.8 | 100.0 | 243.5 | 141.9 | 185.5 | 179.0 | 238.7 | 145.2 |
| % Mortality | 0 | 80 | 0 | 0 | 0 | 0 | 0 | 0 |
| E. brunetti | | | | | | | | |
| % wt. gain to UIC | 100.0 | 34.3 | 87.8 | 40.1 | 39.5 | 92.5 | 96.5 | 61.0 |
| % wt. gain to IC | 291.5 | 100.0 | 255.9 | 116.9 | 115.2 | 274.6 | 281.4 | 178.0 |
| Fecal Score | 0 | 3 | 0 | 3 | 3 | 0 | 0 | 2 |
| E. maxima | | | | | | | | |
| % wt. gain to UIC | 100.0 | 60.0 | 89.5 | 73.3 | 73.8 | 86.7 | 74.8 | 64.3 |
| % wt. gain to IC | 166.7 | 100.0 | 149.2 | 122.2 | 123.0 | 144.4 | 124.6 | 107.1 |
| Fecal Score | 0 | 3 | 0 | 3 | 3 | 1 | 1 | 3 |
| Mixed Infect. 5 supp. | | | | | | | | |
| % wt. gain to UIC | 100.0 | 44.7 | 91.7 | 67.5 | 67.1 | 83.3 | 89.5 | 69.7 |
| % wt. gain to IC | 223.5 | 100.0 | 204.9 | 151.0 | 150.0 | 186.3 | 200.0 | 155.9 |
| % Mortality | 0 | 40 | 0 | 0 | 0 | 0 | 0 | 0 |
| Fecal Score | 0 | 3 | 0 | 2 | 2 | 1 | 1 | 3 |

EXAMPLE VI

The procedures were essentially the same as in Examples II and III, except the E. tenella trial was terminated five days post inoculation and the infected chicks were each given 200,000 sporulated oocysts of E. tenella or 5,300,000 sporulated oocysts of E. acervulina. The results, shown in Table V demonstrate the anticoccidial activity of the test compound, 6-amino-9-( 2,6-dichlorobenzyl)purine, as compared with the commercially available coccidiostats which are identified as compounds B (1-(4-amino-2-N-propyl-5-pyrinidinyl-methyl)-2-picolinium chloride hydrochloride plus methyl-4-acetamide-2-ethoxybenzoate) and D (3,5-dichloro-2,6-dimethyl-4-pyridinol) in Example V.

TABLE V

E. acervulina

| Medication In Diet | Medication % by Wt. of Diet | No. of Chicks | Total Aver. Gain(g) | % wt. Gain To UIC | To IC | Fecal Score |
|---|---|---|---|---|---|---|
| None, UIC | — | 5 | 218 | 100 | 144.4 | 0 |
| None, IC | — | 5 | 151 | 68.8 | 100 | 3 |
| Compound B | 0.0125 | 5 | 221 | 101.4 | 146.4 | 0 |
| Test Compound | 0.0035 | 5 | 223 | 102.3 | 147.7 | 0 |

E. tenella

| Medication In Diet | Medication % by Wt. of Diet | No. of Chicks | Total Aver. Gain(g) | % wt. Gain To UIC | To IC | %Hematocrit | %Mortality |
|---|---|---|---|---|---|---|---|
| None, UIC | — | 5 | 198 | 100 | 176.8 | 33 | 0 |
| None, IC | — | 5 | 112 | 56.5 | 100 | 14 | 60 |

TABLE V-continued

*E. acervulina*

| Medication In Diet | Medication % by Wt. of Diet | No. of Chicks | Total Aver. Gain(g) | % wt. Gain To UIC | % wt. Gain To IC | Fecal Score |
|---|---|---|---|---|---|---|
| Compound D | 0.0125 | 5 | 203 | 102.5 | 181.2 | 33 | 0 |
| Test Compound | 0.0045 | 10 | 197 | 99.5 | 175.9 | 32 | 0 |

EXAMPLE VII

The procedures employed in Example VI were again followed except that 125,000 sporulated oocysts of *E. tenella* were given to the infected chicks. The *E. acervulina* infection was the same. The efficacy of 6-amino-9-(2-chloro-6-fluorobenzyl)purine-$N^1$-oxide (test compound) is compared to that of compound B of Example V against both species. The results are given in Table VI.

TABLE VI

*E. tenella*

| Medication In Diet | Medication % by Wt. of Diet | No. of Chicks | Total Aver. Gain(g) | % wt. Gain To UIC | % wt. Gain To IC | %Hematocrit | %Mortality |
|---|---|---|---|---|---|---|---|
| None, UIC | — | 5 | 189 | 100 | 148.8 | 32 | 0 |
| None, IC | — | 5 | 127 | 67.2 | 100 | 16 | 50 |
| Compound B | 0.0125 | 5 | 186 | 99.6 | 146.6 | 30 | 0 |
| Test Compound | 0.005 | 5 | 203 | 107.4 | 159.8 | 30 | 0 |

*E. acervulina*

| Medication In Diet | Medication % by Wt. of Diet | No. of Chicks | Total Aver. Gain(g) | % wt. Gain To UIC | % wt. Gain To IC | Fecal Score |
|---|---|---|---|---|---|---|
| None, UIC | — | 5 | 224 | 100 | 138.3 | 0 |
| None, IC | — | 5 | 162 | 72.3 | 100 | 3 |
| Compound B | 0.0125 | 5 | 218 | 97.3 | 134.6 | 1 |
| Test Compound | 0.005 | 5 | 211 | 94.2 | 130.2 | 0 |

EXAMPLE VIII

In order to demonstrate the effect of 6-amino-9-(2,6-dichlorobenzyl)purine (Test Compound A) and its corresponding $N^1$-oxide (Test Compound B) on oocysts the following procedures were utilized.

Two groups of five chicks (same type as used in Example II) were each assigned to each of 14 treatments. Feed containing various levels of either of Test Compounds A or B was fed to the birds 24 hours prior to their infection with *E. acervulina*. Unmedicated feed was given to four groups of control chicks for the same period. The procedures employed with both test compounds were identical except for the number of days oocysts were collected; oocysts were collected for five consecutive days for chicks receiving feed containing Test Compound A while oocysts were collected for four consecutive days in the study with Test Compound B. All chicks were inoculated into the crop with 500,000 sporulated oocysts. Total daily fecal collections were initiated on the fifth day after inoculation. The droppings from each group were collected and mixed with a 2.5% aqueous solution of potassium dichromate and homogenized from which a 200 gram aliquot was taken. Total oocyst production of each group was then determined by microscopic counting techniques. The daily samples from the two groups on each treatment were pooled, blended, and sporulated in an additional quantity of 2.5% potassium dichromate solution by bubbling air through each suspension for 48 hours at 28° C. Two series of differential oocyst counts, i.e., sporulated vs. unsporulated, were taken of each treatment microscopically. The results shown in Table VII illustrate the unique inhibitory effect these compounds have on coccidial oocysts of poultry.

TABLE VII

| Medication and % in The Diet | Aver. No. of Oocyst × $10^8$/chick /day | % Oocyst Production To Controls | % of Sample Sporulated | % Sporulation to Controls | Total %+ Reduction of Sporulated Oocysts |
|---|---|---|---|---|---|
| Test Compound A | | | | | |
| None | 35.728 | 100.00 | 36.71 | 100.00 | — |
| 0.0045 | 0.051 | 0.14 | 0 | 0 | 100.00 |
| 0.0035 | 1.200 | 3.36 | 0 | 0 | 100.00 |
| 0.0025 | 9.589 | 26.84 | 2.90 | 7.90 | 97.88 |
| 0.0015 | 16.858 | 47.84 | 5.36 | 11.24 | 94.62 |
| 0.001 | 14.151 | 39.61 | 6.67 | 16.84 | 93.33 |
| Test Compound B | | | | | |
| None | 109.77 | 100.00 | 22.5 | 100.00 | — |
| 0.0065 | 0.33 | 0.30 | 0 | 0 | 100.00 |
| 0.0055 | 0.88 | 0.80 | 0 | 0 | 100.00 |

TABLE VII-continued

| Medication and % in The Diet | Aver. No. of Oocyst × 10⁸/chick /day | % Oocyst Production To Controls | % of Sample Sporulated | % Sporulation to Controls | Total %[+] Reduction of Sporulated Oocysts |
|---|---|---|---|---|---|
| 0.0045 | 0.39 | 0.36 | 0 | 0 | 100.00 |
| 0.0035 | 10.70 | 9.75 | 0.6 | 2.67 | 99.74 |
| 0.0025 | 168.89[++] | 153.82 | 2.1 | 9.33 | 86.65 |
| 0.0015 | 77.35 | 71.38 | 3.1 | 13.78 | 90.16 |
| 0.001 | 107.35 | 97.81 | 6.0 | 26.67 | 73.91 |

[+]100 minus % oocyst production to controls × % Sporulation to controls = total % reduction of sporulated oocysts.
[++]High number possibly due to sampling or counting error.

It will be apparent to one skilled in the art from the foregoing that the novel 6-amino-9-(substituted benzyl)purines and corresponding N¹-oxides of this invention are effective coccidiostats. This is especially apparent from the results of experiments outlined in the foregoing examples. In these tests, the preferred coccidiostat of this invention, i.e., 6-amino-9-(2,6-dichlorobenzyl)purine and its corresponding N¹-oxide, administered to the test chicks in a mash diet was effective in controlling coccidiosis when the chicks were inoculated with sporulated oocysts of species of Eimeria. The test compound was effective against both the cecal form and the intestinal form of coccidiosis. The test compound also compared very favorably with five compounds which are currently commercially available coccidiostats.

Although this invention has been described in relation to specific embodiments, it will be apparent that obvious modifications may be made by one skilled in the art without departing from the intended scope thereof as defined by the appended claims.

We claim:
1. A medicated feed composition for treating coccidiosis comprising a poultry feed ration containing an effective minor amount of a compound of the structural formula:

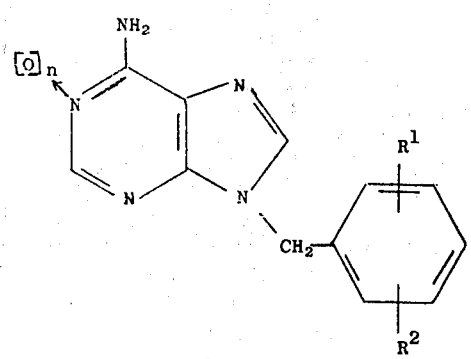

wherein $n$ is 0 or 1, and $R^1$ and $R^2$
  a. individually are of the group consisting of hydrogen, halogen, nitro and trihalomethyl, provided that at least one of $R^1$ and $R^2$ is other than hydrogen, not more than one of $R^1$ and $R^2$ is of the group consisting of nitro and trihalomethyl, and $R^1$ and $R^2$ are located in the 2 and 6 positions on the carbocyclic portion of the compound, or
  b. are both methyl and are located in the 3 and 4 positions on the carbocyclic portion of the compound.

2. A medicated feed composition in accordance with claim 1 wherein said poultry ration contains from about 0.0005 to about 0.05 percent by weight of said compound.

3. A medicated feed composition in accordance with claim 2 wherein $R^1$ and $R^2$ are both methyl and are located in the 3 and 4 positions on the carbocyclic portion of the compound.

4. A medicated feed composition in accordance with claim 3 containing from about 0.0025 to about 0.01 percent by weight of 6-amino-9-(3,4-dimethylbenzene)purine.

5. A medicated feed composition in accordance with claim 3 containing from about 0.0025 to about 0.01 percent by weight of 6-amino-9-(3,4-dimethylbenzene)purine-N¹-oxide.

6. A medicated feed composition in accordance with claim 2 wherein said compound is of the structural formula:

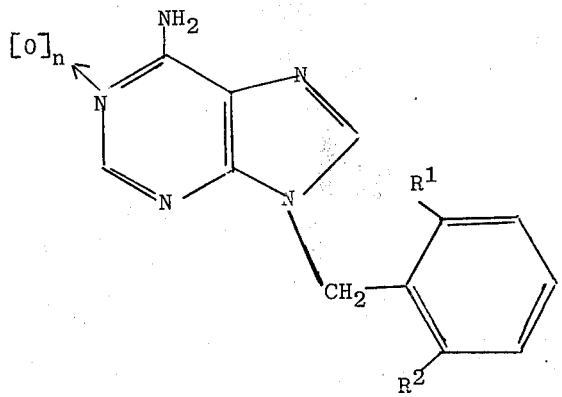

wherein $R^1$ and $R^2$ are individually of the group consisting of nitrogen, halogen, nitro and trihalomethyl, provided that at least one of $R^1$ and $R^2$ is other than hydrogen and not more than one of $R^1$ and $R^2$ is of the group consisting of nitro and trihalomethyl.

7. A medicated feed composition in accordance with claim 6 wherein one of $R^1$ and $R^2$ is hydrogen with the other being halogen.

8. A medicated feed composition in accordance with claim 7 wherein one of $R^1$ and $R^2$ is a halogen selected from the group consisting of chlorine, bromine, and iodine.

9. A medicated feed composition in accordance with claim 8 wherein $n$ is 0.

10. A medicated feed composition in accordance with claim 8 wherein $n$ is 1.

11. A medicated feed composition in accordance with claim 9 containing from about 0.0025 to about 0.01 percent by weight of 6-amino-9-(2-chlorobenzyl)-purine.

12. A medicated feed composition in accordance with claim 10 containing from about 0.0025 to about 0.01 percent by weight of 6-amino-9-(2-chlorobenzyl)-purine-N$^1$-oxide.

13. A medicated feed composition in accordance with claim 9 containing from about 0.0025 to about 0.01 percent by weight of 6-amino-9-(2-bromobenzyl)-purine.

14. A medicated feed composition in accordance with claim 10 containing from about 0.0025 to about 0.01 percent by weight of 6-amino-9-(2-bromobenzyl)-purine-N$^1$-oxide.

15. A medicated feed composition in accordance with claim 9 containing from about 0.0025 to about 0.01 percent by weight of 6-amino-9-(2-iodobenzyl)-purine.

16. A medicated feed composition in accordance with claim 10 containing from about 0.0025 to about 0.01 percent by weight of 6-amino-9-(2-iodobenzyl)-purine-N$^1$-oxide.

17. A medicated feed composition in accordance with claim 6 wherein both R$^1$ and R$^2$ are halogen.

18. A medicated feed composition in accordance with claim 17 wherein $n$ is 0.

19. A medicated feed composition in accordance with claim 17 wherein $n$ is 1.

20. A medicated feed composition in accordance with claim 18 containing from about 0.0025 to about 0.01 percent by weight of 6-amino-9-(2,6-dichlorobenzyl)purine.

21. A medicated feed composition in accordance with claim 19 containing from about 0.0025 to about 0.01 percent by weight of 6-amino-9-(2,6-dichlorobenzyl)purine-N$^1$-oxide.

22. A medicated feed composition in accordance with claim 18 containing from about 0.0025 to about 0.01 percent by weight of 6-amino-9-(2-chloro-6-fluorobenzyl)purine.

23. A medicated feed composition in accordance with claim 19, containing from about 0.0025 to about 0.01 percent by weight of 6-amino-9-(2-chloro-6-fluorobenzyl)purine-N$^1$-oxide.

24. A medicated feed composition in accordance with claim 18 containing from about 0.0025 to about 0.1 percent by weight of 6-amino-9-(2-chloro-6-iodobenzyl)purine.

25. A medicated feed composition in accordance with claim 19 containing from about 0.0025 to about 0.1 percent by weight of 6-amino-9-(2-chloro-6-iodobenzyl)purine-N$^1$-oxide.

26. A medicated feed composition in accordance with claim 18 containing from about 0.0025 to about 0.1 percent by weight of 6-amino-9-(2-chloro-6-bromobenzyl)purine.

27. A medicated feed composition in accordance with claim 19 containing from about 0.0025 to about 0.01 percent by weight of 6-amino-9-(2-chloro-6-bromobenzyl)purine-N$^1$-oxide.

28. A medicated feed composition in accordance with claim 6 wherein one of R$^1$ and R$^2$ is hydrogen with the other being trihalomethyl.

29. A medicated feed composition in accordance with claim 28 wherein $n$ is 0.

30. A medicated feed composition in accordance with claim 29 containing from about 0.0025 to about 0.01 percent by weight of 6-amino-9-(2-trifluoromethylbenzyl)purine.

31. A medicated feed composition in accordance with claim 28 wherein $n$ is 1.

32. A medicated feed composition in accordance with claim 31 containing from about 0.0025 to about 0.01 percent by weight of 6-amino-9-(2-trifluoromethylbenzyl)purine-N$^1$-oxide.

33. A medicated feed composition in accordance with claim 6 wherein one of R$^1$ and R$^2$ is hydrogen with the other being nitro.

34. A medicated feed composition in accordance with claim 33 containing from about 0.0025 to about 0.01 percent by weight of 6-amino-9-(2-nitrobenzyl)-purine.

35. A medicated feed composition in accordance with claim 33 containing from about 0.0025 to about 0.01 percent by weight of 6-amino-9-(2-nitrobenzyl)-purine-N$^1$-oxide.

36. The method of controlling coccidiosis in poultry which comprises orally administering to poultry an anti-coccidially-effective quantity of a compound of the formula:

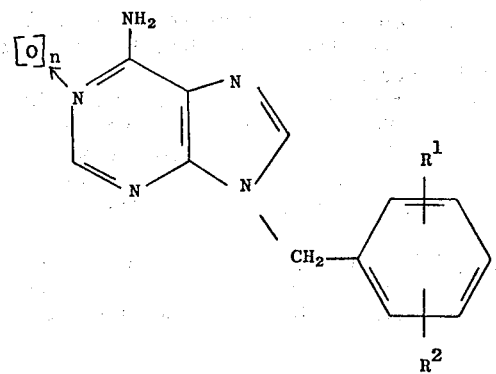

wherein $n$ is 0 or 1, and R$^1$ and R$^2$
 a. individually are of the group consisting of hydrogen, halogen, nitro and trihalomethyl, provided that at least one of R$^1$ and R$^2$ is other than hydrogen, not more than one of R$^1$ and R$^2$ is of the group consisting of nitro and trihalomethyl, and R$^1$ and R$^2$ are located in the 2 and 6 positions on the carbocyclic portion of the compound, or
 b. are both methyl and are located in the 3 to 4 positions on the carbocyclic portion of the compound.

37. A method in accordance with claim 36 wherein said poultry is fed a ration containing from about 0.0005 to about 0.5 percent by weight of said compound.

38. A method in accordance with claim 37 wherein said poultry is fed a ration containing from about 0.0025 to about 0.01 percent by weight of said compound and R$^1$ and R$^2$ are both methyl and are located in the 3 and 4 positions on the carbocyclic portion of the compound.

39. A method in accordance with claim 37 wherein said compound is of the structural formula:

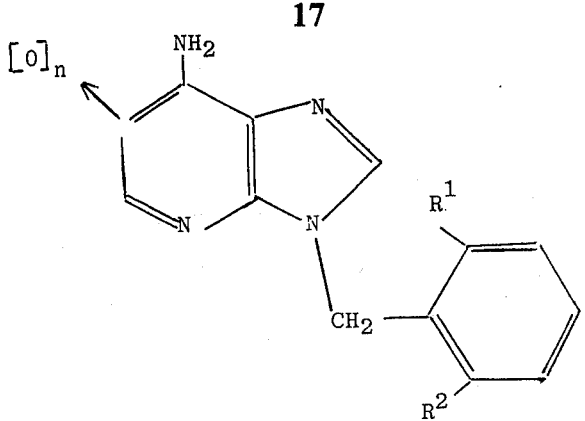

wherein R¹ and R² are individually of the group consisting of nitrogen, halogen, nitro and trihalomethyl, provided that at least one of R¹ and R² is other than hydrogen and not more than one of R¹ and R² is of the group consisting of nitro and trihalomethyl.

40. A method in accordance with claim 39 wherein said poultry is fed a ration containing from about 0.0025 to about 0.1 percent by weight of said compound, and one of R¹ and R² is hydrogen with the other being halogen.

41. A method in accordance with claim 39 wherein said poultry is fed a ration containing from about 0.0025 to about 0.01 percent by weight of said compound, and both R¹ and R² are halogen.

42. A method in accordance with claim 39 wherein said poultry is fed a ration containing from about 0.0025 to about 0.01 percent by weight of said compound, and one of R¹ and R² is hydrogen with the other being trihalomethyl.

43. A method in accordance with claim 39 wherein said poultry is fed a ration containing from about 0.0025 to about 0.01 percent by weight of said compound, and one of R¹ and R² is hydrogen with the other being nitro.

\* \* \* \* \*

UNITED STATES PATENT OFFICE
CERTIFICATE OF CORRECTION

PATENT NO. : 3,953,597

DATED : April 27, 1976

INVENTOR(S) : Emil P. Lira, Walter M. Barker, Robert C. McCrae

It is certified that error appears in the above-identified patent and that said Letters Patent are hereby corrected as shown below:

Column 5, line 31, between "minimum" and "is", insert --amount--.
Column 7, line 6, delete "to". Column 10, line 7, after "weight gains" insert -- along --; and Table IV beginning after line 12, "Mixed Infect. 5 supp." in line 22 of the extreme left-hand column should read --Mixed Infect. 5 spp--; and "96.8" in line 1 of Column "B" should read --96.6--; line 50, between "chloride" and "hydrochloride", insert -·-. Column 11, "Table V-continued" should appear as follows:

E. tenella

| Medication In Diet | Medication % by Wt. of Diet | No. of Chicks | Total Aver. Gain(g) | % wt. To UIC | Gain To IC | % Hematocrit | % Mortality |
|---|---|---|---|---|---|---|---|
| Compound D | 0.0125 | 5 | 203 | 102.5 | 181.2 | 33 | 0 |
| Test Compound | 0.0045 | 10 | 197 | 99.5 | 175.9 | 32 | 0 |

Column 12, line 44, "of" should read --for--.

Claim 25, Column 15, line 54, "0.1" should read --0.01--.
Claim 26, Column 15, line 58, "0.1" should read --0.01--.
Claim 36, Column 16, line 55, "to" should read ---and--.
Claim 37, Column 16, line 59, "0.5" should read --0.05--.
Claim 40, Column 18, line 3, "0.1" should read --0.01--.

Signed and Sealed this

First Day of February 1977

[SEAL]

Attest:

RUTH C. MASON
Attesting Officer

C. MARSHALL DANN
Commissioner of Patents and Trademarks